United States Patent

Hackl et al.

[11] Patent Number: 5,414,083
[45] Date of Patent: May 9, 1995

[54] METHOD FOR THE PRODUCTION OF N-CYCLIC AND N,N'-DICYCLIC UREAS AND THEIR USE AS CHEMICAL SOLVENTS

[75] Inventors: Kurt A. Hackl; Markus Rössler; Martin Müllner, all of Linz; Gerhard Stern, Sonnberg, all of Austria

[73] Assignee: Chemie Linz Gesellschaft m.b.H., Linz, Austria

[21] Appl. No.: 185,246

[22] Filed: Jan. 24, 1994

[30] Foreign Application Priority Data

Jan. 22, 1993 [AT] Austria ........................... 9493

[51] Int. Cl.$^6$ .................. C07D 413/02; C07D 401/02; C07D 403/02; C07D 211/02
[52] U.S. Cl. ........................ 544/130; 544/141; 546/208; 546/245; 548/524; 548/538
[58] Field of Search ............... 544/130, 141; 546/190, 546/208, 245; 548/524, 538

[56] References Cited

U.S. PATENT DOCUMENTS

| | | | |
|---|---|---|---|
| 4,835,312 | 5/1989 | Itoh | 564/205 |
| 5,169,954 | 12/1992 | Hackl et al. | 544/169 |
| 5,218,002 | 6/1993 | Stroech | 514/919 |

FOREIGN PATENT DOCUMENTS

| | | |
|---|---|---|
| 923967 | 2/1955 | Germany . |
| 1105866 | 8/1959 | Germany . |
| 4018070A1 | 12/1991 | Germany . |
| 4-8425 | 11/1989 | Japan . |
| 1369248 | 10/1974 | United Kingdom . |

OTHER PUBLICATIONS

E. Müller, Houben–Weyl, 4th edition, vol. E4, pp. 335 to 367, with partial English translation (1983).
Chemical Abstracts vol. 112, 198399j (1990) with English Translation of Examples 7 and 8 of abstracted patent (JP-B-4-8425).
Chemical Abstracts vol. 104, 58816c (1986).
Beilstein's Handbuch der organischen Chemie, 4. Auflage, vol. 20, E1, p. 16 (1935).

*Primary Examiner*—Peter O'Sullivan
*Attorney, Agent, or Firm*—Wenderoth, Lind & Ponack

[57] ABSTRACT

A process for the dissolution of chemical compounds by use of ureas in which at least one of the urea's two nitrogen atoms is part of a non-aromatic ring which can be broken by an oxygen or sulphur atom as a chemical solvent, and a method of producing tri- or tetraalkylated ureas or bis ureas wherein at least one of the urea's nitrogen atoms is part of a non-aromatic ring which can be broken by an oxygen or sulphur atom by means of dialkylating the —NH$_2$ group of a urea with an alkene or alkene arylene alkene dihalogenide, disulphonate or dihydrogen sulphonate in the presence of a solid base and a phase-transfer catalyst.

5 Claims, No Drawings

METHOD FOR THE PRODUCTION OF N-CYCLIC AND N,N'-DICYCLIC UREAS AND THEIR USE AS CHEMICAL SOLVENTS

In general, chemical reactions are carried out in a solvent and diluting agent, as the direct combination of reaction partners does not normally allow for control over the reactions and many reactions take their course only when the reaction partners are dissolved. The requirements of a solvent to be used for chemical reactions are high thermal stability, good distillability, colorlessness, nonpoisonousness, inertness with regard to the reactants, mixability with other solvents, and above all, the ability to easily dissolve both polar or hydrophile and non-polar or hydrophobic compounds. Hardly any solvents exist, however, which fulfill all these requirements.

It is known from E. Muller, Houben-Weyl, 4th Edition, Volume E4, page 335 that tetraalkylated ureas such as tetramethyl urea and tetraethyl urea or N,N' bridged ureas such as 1,3-dimethyl-2-oxo-imidazolidine, 1,3-dimethyl-2-imidazolidinone or 1,3-dimethyl-2-oxohexahydropyrimidine are used as aprotic solvents for technical purposes because of their favorable qualities.

It was found unexpectedly that ureas with different chemical structures, namely tetraalkylated N-cyclic or N,N'-dicyclic ureas, and especially N-substituted 1-pyrrolidine, 1-piperidine or 1-morpholine carboxylic acid amide derivatives are generally in a liquid state, have high thermal stability and good distillability, are nonpoisonous and completely inert with regard to functional groups, and represent all-purpose and excellent solvents for various reactions and applications, both with polar or hydrophile and non-polar or hydrophobic compounds. It was shown unexpectedly that, despite their high hydrophobic proportion, such ureas can also be mixed with water in addition to other organic solvents. Furthermore, these ureas possess an excellent ability to dissolve strongly polar or ionic compounds, e.g. salts. Since organic solvents are usually not able to dissolve strongly polar or ionic compounds, this surprising effect can be used, for example, for reactions with salts in a nonaqueous medium.

Object of the invention is therefore a process for the dissolution of a chemical compound by a chemical solvent, comprising using as chemical solvent at least one urea of the general formula

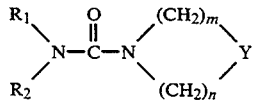   I in which $R_1$ and $R_2$ independently of one another denote a straight-chain, branched or cyclic alkyl group having 1 to 22 C atoms, which is unsubstituted or substituted by fluorine atoms; nitro groups; alkenyl- or alkyliden groups having 2 to 6 C atoms; phenyl groups which are unsubstituted or substituted by fluorine atoms, nitro groups, alkyl groups having 1 to 5 C atoms, alkoxy groups having 1 to 5 C atoms or phenoxy groups; benzyl or phenylethyl groups which are unsubstituted or substituted by fluorine atoms, nitro groups, alkyl groups having 1 to 5 C atoms, alkoxy groups having 1 to 5 C atoms or phenoxy groups; alkoxy groups having 1 to 5 C atoms; phenoxy groups which are unsubstituted or substituted by fluorine atoms, nitro groups, alkyl groups having 1 to 5 C atoms, alkoxy groups having 1 to 5 C atoms or phenoxy groups; or, together with the nitrogen atom, a five or six-member non-aromatic ring which can be broken by an oxygen or sulphur atom; n and m represent independently of one another the numbers 1 to 3, whereby n plus m represent the numbers 3 or 4.

Alkyl groups are to be understood as those alkyl groups with 1 to 22, preferably with 1 to 10 C atoms, more preferably with 1 to 8, and most preferably with 1 to 6 C atoms, e.g. ethyl, propyl, isopropyl, tertiary butyl, isopentyl, methylcyclopentyl, cyclohexyl, 2-ethylhexyl, octyl, decyl, dodecyl, hexadecyl, or octadecyl groups. The alkyl groups can be unsubstituted or substituted by fluorine atoms, nitro groups, alkenyl- or alkyliden groups having 2 to 6 C atoms; phenyl groups which are unsubstituted or substituted by fluorine atoms, nitro groups, alkyl groups having 1 to 5 C atoms, alkoxy groups having 1 to 5 C atoms or phenoxy groups, preferred unsubstituted phenyl groups: or alkoxy groups with 1 to 5 C atoms, e. g. methoxy, ethoxy, isopropoxy, butoxy or phenoxy groups. Alkyl groups are preferable when unsubstituted. Benzyl or phenylethyl groups can be unsubstituted or substituted by alkyl groups with 1 to 5 C atoms, e.g. ethyl, isopropyl, isopentyl, alkoxy groups with 1 to 5 C atoms, e.g. methoxy, ethoxy. isopropoxy, or butoxy groups, fluorine atoms or nitro groups. Preferred are unsubstituted benzyl or phenylethyl groups.

$R_1$ and $R_2$ can also form together with the nitrogen atom a five or six-member non-aromatic ring which can be broken by an oxygen or sulphur atom, i.e. an oxazolidine, pyrrolidine, piperidine, morpholine, thiomorpholine or thiazolidine ring, for example.

Preferably, $R_1$ and $R_2$ represent independently of one another an unsubstituted straight-chain or branched alkyl group with 1 to 10 C atoms, or $R_1$ and $R_2$ represent together with the nitrogen atom a non-aromatic ring which can be broken by an oxygen or sulphur atom, preferably a pyrrolidine, piperidine or morpholine ring.

Y represents a methylene group, an oxygen or sulphur atom, preferably a methylene group or an oxygen atom, and m and n represent independently of one another the numbers 1 to 3, preferably 1 to 2, whereby the sum of m plus n represents the numbers 3 or 4.

Methods for the production of ureas are disclosed, for example, in U. Petersen in E. Müllner, Houben-Weyl, 4th Edition, Volume E4, pages 336 ff. U.S. Pat. No. 4,835,312 contains a description of the fact that amide compounds, among which ureas are also understood, can be alkylated in an aprotic, polar diluting agent at the nitrogen atom or at both nitrogen atoms by means of simultaneous contact and conversion of a strongly basic substance with the amide compound and a halogen-substituted compound when the reaction is started as long as the basic substance is in a suspended state. However, this method is suitable only for the production of symmetrical, if necessary substituted, methyl ureas based on urea, and not for the production of N-cyclic or N,N'-dicyclic ureas.

In JP-B-4-8425 (Chemical Abstracts Volume 112, 198399), examples 7 and 8 is indicated, that 1,1-carbonyl bispyrrolidine respectively 1,1-carbonyl bispiperidine might be produced by reaction of urea with 1,4-dibrombutane respectively with 1,5-dibrompentane in the presence of KOH in N,N-dimethylformamide respectively in 1,3-dimethylimidazolidinone as solvent. However it was proved, that in fact absolutely no N,N'-dicyclic urea originate from the reaction according to the method of examples 7 or 8 of JP-B-4-8425.

Unexpectedly, it was found that the free amino group present in a urea in which one of the two amino groups is alkylated can be dialkylated with a difunctional alkene group, whereby an N-cyclic urea is formed without N,N' bridges appearing when a phase-transfer catalyst is employed. The new method is not only suitable for the production of tetraalkylated N-cyclic or N,N'-dicyclic ureas of Formula I, but also for the production of trialkylated N-cyclic urea derivatives or N-cyclic bis ureas.

The object of the invention is therefore also a method for the production of ureas of the General Formula

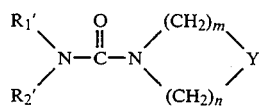

in which Y, m and n have the meanings described in claim 1, and $R_1'$ and $R_2'$ have the meanings of $R_1$ and $R_2$ described in claim 1, and $R_1'$ additionally represents hydrogen, or $R_1'$ represents hydrogen and $R_2'$ represents a group of the Formula

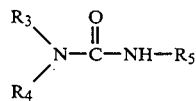

in which $R_3$ and $R_4$ have the meanings of $R_1$ and $R_2$ described in claim 1, whereby $R_3$ and $R_4$ additionally represent hydrogen, and $R_5$ represents an alkylene group with 2 to 20 C atoms or an alkylene phenylene alkylene group, the alkylene groups having independently of one another 1 to 3 C atoms comprising reacting a urea or a bis urea of the General Formula

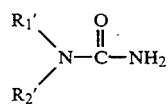

in which $R_1'$ and $R_2'$ have the meanings described above, in the presence of a solid base and a phase-transfer catalyst in a diluting agent which is inert under reaction conditions at temperatures of 0° to 150° C. with a compound of the General Formula

X—R_6—X    V in which $R_6$ represents a straight-chain alkene group with 4 or 5 C atoms in which the atom in the 2 or 3 position can be replaced by an oxygen or sulphur atom and X represents a halogen, sulphonic acid, or hydrogen sulphate group, whereby the —$NH_2$ group of the urea of the General Formula IV is dialkylated through elimination of both hydrogen atoms by the compound of the General Formula V through the elimination of the X leaving groups by ring closure.

In the compound of the General Formula II, $R_1'$ and $R_2'$ have the meanings described above for $R_1$ and $R_2$, whereby $R_1'$ additionally represents hydrogen or, in the event that the compound of Formula II is a bis urea $R_1'$ represents a hydrogen atom and $R_2'$ represents a group of the General Formula III.

In the compound of the General Formula III, $R_3$ and $R_4$ have the meaning of $R_1$ and $R_2$ described in claim 1, whereby $R_3$ and $R_4$ additionally represent hydrogen and $R_5$ represents an alkene group with 2 to 20 C atoms, preferably with 2 to 8, for example ethylene, hexylene, dodecyl groups or an alkene phenylene alkene group in which the expression alkene preferably represents low alkene groups with 1 to 3 C atoms, for example xylylene groups.

Ureas or bis ureas of the General Formula IV, in which $R_1'$ and $R_2'$ have the meanings described above, can be produced according to the normal, known method, e.g. by converting urea or isocyuranic acid with a suitable amine.

Solid bases such as alkali hydroxides, e.g. potassium hydroxide, sodium hydroxide or alkali amides, e.g. sodium amide or potassium amide, are suitable. Preferably, alkali hydroxides are employed, whereby the alkali hydroxide can contain a low concentration of a carbonate such as potassium carbonate or sodium carbonate amounting to 2 to 20 mole % in relation to the alkali hydroxide. The base is used in solid, powdered form or in the form of pellets in excess in relation to the urea of Formula IV which is employed. Preferably, 1.5 to 10 mole are employed per mole of the urea of Formula IV; more preferably, 3 to 5 mole of the solid base are employed.

Common phase-transfer catalysts are suitable as a catalyst. An abstract of suitable phase-transfer catalysts and their possible employment is disclosed in W. E. Keller: Phasetransfer reactions (Fluka Compendium, Vol. 1, 2 and 3; Georg Thieme Verlag, Stuttgart—New York, 1986, 1987 and 1992). Preferably, quaternary ammonium salts such as tetrabutyl ammonium hydrogen sulphate, tetrabutyl ammonium chloride or benzyl triethyl ammonium chloride are employed as phase-transfer catalysts.

In the Compound of the General Formula V, $R_6$ represents a straight-chain alkene group with 4 or 5 C atoms in which one of the C atoms in the 2 or 3 position can be replaced by an oxygen or sulphur atom, preferably an oxygen atom.

X represents a halogen atom (especially chlorine, bromide or iodine should be understood by halogen), a sulphonic-acid group or a hydrogen sulphate group, preferably a halogen atom.

The compounds of Formula V are generally employed equimolar to the urea of Formula IV in so far as the urea of Formula IV is not a bis urea or in so far as the urea of Formula IV is a bis urea in which only one of the two —$NH_2$ groups are to be dialkylated. If both —$NH_2$ groups in a bis urea of Formula IV in which $R_3$ and $R_4$ represent hydrogen are to be dialkylated, generally two equivalents of a compound of Formula V are employed per equivalent of bis urea. In certain cases, however, an excess of one or the other reaction partners can be useful. It was determined that, in certain cases, the yield can be increased when 0.5 to 3 equivalents of the compound of Formula V are employed per —$NH_2$ group in the urea of Formula IV.

Diluting agents which are inert under the reaction conditions and which are solvents for the urea of Formula IV and/or the compound of Formula V are used as diluting agents. These are aromatic hydrocarbons, e.g. benzole, toluene, xylenes, higher aliphatic hydrocarbons, e.g. paraffins, aromatic halogenated hydrocarbons, e.g. chlorobenzene, trichlorobenzene, ether, e.g. tetrahydrofuran or dimethyl sulfoxide, or mixtures of such diluting agents. Preferably, aromatic hydrocarbons are employed; toluene is employed more preferably.

For the execution of the method according to the invention, the urea of Formula IV is dissolved in a diluting agent which can be predried before being employed. The solid base is added in the form of pellets or in powdered form and well suspended by stirring vigorously, after which the catalyst is introduced. The compound of Formula V can be added to this mixture, which is stirred vigorously and heated if necessary, before heating, or it can be added to the already heated mixture.

The reaction mixture is heated if necessary to a temperature of up to approximately 150° C., preferably to 70° to 150° C., more preferably to the reflux temperature of the diluting agent employed. When this is done, the —$NH_2$ group of the urea of Formula IV is dialkylated by the compound of Formula V through elimination of both X leaving groups and both hydrogen atoms of the —$NH_2$ group, and the urea of the General Formula II is produced. Unexpectedly, hardly any N,N' bridges or bonds of 2 moles of the urea of the General Formula IV result.

After the conversion has been completed, the reaction mixture is either allowed to chill and filtered and the liquid residue is distilled or chromatographed, or water is added to the reaction mixture and the urea of Formula II is extracted from the reaction mixture with the aid of an extracting agent. Water-inmiscible organic extracting agents such as hydrocarbons, e.g. hexane, heptane, halogenated hydrocarbons, e.g. methylene chloride, chloroform or ether, e.g. diethyl ether, diisopropyl ether, carboxylic acid ether, e.g. ethyl acetate, butyl acetate are employed. The organic phase is washed with water and dried and the diluting agent is evaporated, whereby the mixture can be afterdried in vacuo.

In general, the purity of the urea of Formula II produced in this way is sufficient. If necessary, it may be purified afterwards, e.g. by means of chromatography or distillation.

In a preferred embodiment, a urea of the Formula IV in which $R_1'$ and $R_2'$ represent independently of one another an alkyl group with 1 to 10 C atoms and $R_1'$ additionally represents hydrogen, or $R_1'$ and $R_2'$ represent a pyrrolidine, piperidine or morpholine ring together with the nitrogen atom, is dissolved in toluene, and 3 to 5 equivalents of potassium or sodium hydroxide pellets containing 4 to 10 mole % of potassium or sodium carbonate, and 0.04 to 0.06 equivalents of a quaternary ammonium salt as a phase-transfer catalyst, are added while stirring vigorously, distilled to reflux, to which 1,4-butane dihalide or 1,5-pentane dihalide in which one of the C atoms can be replaced by an oxygen atom in the 2 or 3 position is added. After the reaction is complete, water is added to the reaction mixture which is then extracted several times with methylene chloride and/or chloroform. The combined organic phases are washed with water and dried, the diluting agent is evaporated, and afterdrying is performed in vacuo.

A good yield of high purity N-cyclic or N,N'-dicyclic ureas is produced from non-poisonous raw materials according to the described method.

EXAMPLE 1

3.56 g of N-piperidine carboxylic acid amide (0.02 mole) was dissolved in 40 ml of toluene, mixed with 4.48 g of KOH (0.08 mole), 0.28 g of tetrabutyl ammonium chloride (1 mmole) and 2.16 g of 1,4-dibromobutane (0.01 mole) at room temperature and distilled to reflux while being stirred vigorously. The course of the reaction was observed with the aid of $^1$H—NMR. After 2 hours, the reaction was complete, and the reaction mixture was poured into water. The aqueous mixture was then extracted several times with methylene chloride, and the organic phase was dried and evaporated. When this was done, 1.73 g, i.e. 95% of the theory, of 1-piperidino-1-pyrrolidine carbonyl, relative to the 1,4-dibromobutane employed, was obtained.

$^1$H—NMR (300 MHz, CDCl$_3$, delta): 3.35 ppm (t, py-1,4; J=5.6 Hz); 3.18 ppm (t, pip-1,5; J=6.7 Hz); 1.81 ppm (m; py-2,3); 1.57 ppm (m; pip-2,3,4)

$^{13}$C—NMR (70 MHz, CDCl$_3$, delta): 163.53 ppm (C=O); 48.38 ppm (py-1,4); 47.45 ppm (pip-1,5); 25.90 ppm (pip-2,4); 25.57 ppm (py-2,3); 24.57 ppm (pip-3).

EXAMPLES 2–11

The following examples 2–11 were performed in the manner described in Example 1 and using the same amount of KOH and catalyst per mole of urea of the Formula IV; however, different ureas of Formula IV and different compounds of Formula V in different molar ratios were used. The results are abstracted in Table 1. The reaction time amounted to approximately 2 hours each.

TABLE 1

| No. | IV-$R_1'$ | IV-$R_2'$ | V-$R_6$ | V-X | IV:V | A % |
|---|---|---|---|---|---|---|
| 2 | $C_2H_5$— | $C_2H_5$— | —$(CH_2)_4$— | Br | 2:1 | 65 |
| 3 | $C_2H_5$— | $C_2H_5$— | —$(CH_2)_4$— | Br | 1:1 | 53 |
| 4 | —$(CH_2)_4$— | | —$(CH_2)_4$— | Br | 2:1 | 71 |
| 5 | —$(CH_2)_4$— | | —$(CH_2)_5$— | Br | 2:1 | 50 |
| 6 | —$(CH_2)_5$— | | —$(CH_2)_4$— | Cl | 2:1 | 73 |
| 7 | —$(CH_2)_5$— | | —$(CH_2)_5$— | Br | 2:1 | 61 |
| 8 | —$(CH_2)_2$—O—$(CH_2)_2$— | | —$(CH_2)_4$— | Br | 1:1 | 76 |
| 9 | —$(CH_2)_2$—O—$(CH_2)_2$— | | —$(CH_2)_4$— | Br | 2:1 | 80 |
| 10 | —$(CH_2)_2$—O—$(CH_2)_2$— | | —$(CH_2)_5$— | Br | 2:1 | 65 |
| 11 | H | $C_4H_9$— | —$(CH_2)_4$— | Br | 2:1 | 67 |

Characteristic data:

EXAMPLES 2 AND 3

$^1$H—NMR (300MHz, CDCl$_3$, delta): 3.257 ppm (t, py-1, $J_{CH2CH2}$=6.6 HZ); 3.126 ppm (q; ethyl-1; $J_{CH2CH3}$=5.3 Hz); 1.742 ppm (m; py-2,3); 1.048 ppm (t, ethyl-2; $J_{CH2CH3}$=6.6 HZ)

$^{13}$C—NMR (70 MHz, CDCl$_3$, delta): 163.01 ppm (C=O); 48.68 ppm (py-1,4); 42.00 ppm (ethyl-1); 25.87 ppm (ethyl-2); 13.78 ppm (py-2,3)

EXAMPLE 4

$^1$H—NMR (300MHz, CDCl$_3$, delta ): 3.36 ppm (t; N—$CH_2$; J=5.5 Hz ); 1.83 ppm (m; $CH_2$—$CH_2$)

$^{13}$C—NMR (70 MHz, CDCl$_3$, delta): 161.0 ppm (C=O); 47.7 ppm (N—$CH_2$); 25.1 ppm ($CH_2$—$CH_2$)

EXAMPLES 5 AND 6

Characteristic data same as described in Example 1.

EXAMPLE 7

$^1$H—NMR (300MHz, CDCl$_3$, delta): 3.16 ppm (t; pip-1,5; J=5.7); 1.57 ppm (m; pip-2,3,4)

$^{13}$C—NMR (70 MHz, CDCl$_3$, delta): 164.75 ppm (C=O); 48.13 ppm (pip-1,5); 25.71 ppm (pip-2,4); 24.99 ppm (pip-3)

EXAMPLES 8 AND 9

$^{1}$H—NMR (300MHz, CDCl$_3$, delta ): 3.67 ppm (t; mor-O-CH$_2$; J=4.7 Hz); 3.37 ppm (t; pyr-N-CH$_2$; J=6.7 Hz); 3.26 ppm (t; mor-N-CH$_2$; J=4.7 Hz) 1.84 ppm (m; pyr-N-CH$_2$—CH$_2$)

$^{13}$C—NMR (70 MHz, CDCl$_3$, delta): 162.58 ppm (C=O); 66.71 ppm (mor-O-CH$_2$); 48.25 ppm (pyr-N-CH$_2$); 46.78 ppm (mor-N-CH$_2$); 25.51 ppm; (pyr-2,3)

EXAMPLE 10

$^{1}$H—NMR (300MHz, CDCl$_3$, delta): 3.66 ppm (t; mor-O-CH$_2$; J=4.8 Hz ); 3.22 ppm (m; pip-1,5 and mor-N-CH$_2$) 1.57 ppm (m; pip-2,3,4)

$^{13}$C—NMR (70 MHz, CDCl$_3$, delta): 164.56 ppm (C=O); 67.00 ppm (mor-O-CH$_2$); 48.33 ppm (pip-N-CH$_2$); 47.86 ppm (mor-N-CH$_2$); 26.10 ppm; (pip-2,4); 24.57 ppm (pip-3)

EXAMPLE 11

$^{1}$H—NMR (200MHz, CDCl$_3$, delta): 4.390 ppm (t; NH; J=5.8 Hz); 3.340 ppm (t; N—CH$_2$; J$_{12}$=6.7 Hz); 3.222 ppm (dt; HN—CH$_2$; J$_{CH2NH}$=5.8 HZ; J$_{CH2CH2}$=7.0 HZ) 1.893 ppm (tt; pyr-2,3; J$_{12}$=6.7 Hz; J$_{23}$=3.5 Hz); 1.536-1.288 ppm (m; but-2,3); 0.921 ppm (t; but-CH$_3$; J$_{CH2CH3}$=7.1 HZ)

$^{13}$C—NMR (50 MHz, CDCl$_3$, delta): 156.016 ppm (C=O); 45.41 ppm (pyr-1,4); 40.28 ppm (but-1); 32.61 ppm (but-2); 25.52 ppm (pyr-2,3); 20.03 ppm (but-3); 13.78 ppm; (but-4)

EXAMPLE 12

22.8 g of pyrrolidine carboxylic acid amide (0.2 mole) was dissolved in 400 ml of toluene, mixed with 56 g of KOH (0.8 mole), 2.78 g of tetrabutyl ammonium chloride (1 mmole) and 21.6 g of 1,4-dibromobutane (0.1 mole) at room temperature and distilled to reflux while being stirred vigorously. The reaction was observed with the aid of $^{1}$H—NMR. After the reaction was complete, the diluting agent was evaporated and the residue was distilled in a vacuum. When this was done, 8.27 g of 1,1-carbonyl bispyrrolidine, i.e. 54 % of the theory and relative to the 1,4-dibromobutane employed, was obtained.

Characteristic data same as described in Example 4.

EXAMPLES 13–16

Examples 13–16 were conducted in the manner described in Example 12 with the same amounts of KOH and catalyst; however, eight times the molar amount of KOH relative to the applied compound of Formula V was employed in Example 13, and in Example 14, the compound of Formula V was added by drops in the refluxing mixture of urea of Formula I, toluene, base and catalyst. The reaction times amounted to approximately 2 hours each with the exception of Example 15. The reaction time of Example 15 amounted to 0.15 hours. The results are abstracted in Table 2.

| No. | IV-R$_1$'-R$_2$' | V-R$_6$ | V-X | IV:V | A % |
|---|---|---|---|---|---|
| 13 | —(CH$_2$)$_4$— | —(CH$_2$)$_4$— | Br | 1:1 | 65 |
| 14 | —(CH$_2$)$_4$— | —(CH$_2$)$_4$— | Br | 1:1 | 59 |
| 15 | —(CH$_2$)$_4$— | —(CH$_2$)$_4$— | Br | 1:1 | 67 |

-continued

| No. | IV-R$_1$'-R$_2$' | V-R$_6$ | V-X | IV:V | A % |
|---|---|---|---|---|---|
| 16 | —(CH$_2$)$_4$— | —(CH$_2$)$_4$— | Br | 1:3 | 72 |

Characteristic data same as described in Example 4.
In tables 1 and 2, the following symbols represent:
No.: Number of the example and the compound
IV—R$_1$': R$_1$' in Formula IV
IV—R$_2$': R$_2$' in Formula IV
V—R$_6$: R$_6$ in Formula V
V—X: X in Formula V
IV:V: Molar ratio of the compounds in formulas IV and V
A%: Yield in mole per cent relative to the applied compound of Formula V. The yield is relative to the applied compound of Formula IV in Example 16 only.

COMPARATIVE EXAMPLES

EXAMPLE 7 OF JP-B-4-8425

13 g of urea in 150 ml of N,N-dimethylformamide were stirred together with 96 g of 1,4-dibrombutane and 50 g of potassium hydroxide at a temperature of 20° C. over a period of 4 hours: After that the non-soluble parts were removed by filtration and the filtrate was distilled. Four fractions between 23° and 80° C. (0.4 mm Hg) were received, which were analyzed using $^{1}$H—NMR spectroscopy. Thereby only 1,4-dibrombutane and N,N-dimethylformamide but absolutely no 1,1-carbonyl bispyrrolidine were found.

EXAMPLE 8 OF JP-B-4-8425

13 g of urea in 150 ml of 1,3-dimethyl-2-imidazolidinone were stirred together with 150 g of 1,5-dibrompentane and 50 g of potassium hydroxide at a temperature of 20° C. over a period of 4 hours. After that the non-soluble parts were removed by filtration and the filtrate was distilled. Four fractions between 23° and 76° C. (0.35 mm Hg) were received, which were analyzed using $^{1}$H—NMR spectroscopy. Thereby only 1,5-dibrompentane and 1,3-dimethyl-2-imidazolidinone but absolutely no 1,1-carbonyl bispiperidine were found.

What we claim is:
1. A method for the production of ureas of the formula:

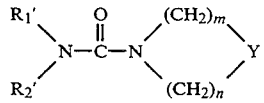

in which Y represents a methylene group or an oxygen atom, m and n representing independently of one another the numbers 1 to 3, whereby n plus m represent the numbers 3 or 4, R$_1$' and R$_2$' independently of one another denote a straight-chain, branched or cyclic alkyl group having 1 to 22 C atoms, which is unsubstituted or substituted by fluorine atoms; nitro groups; alkenyl- or alkylidene groups having 2 to 6 C atoms; phenyl groups which are unsubstituted or substituted by fluorine atoms, nitro groups, alkyl groups having 1 to 5 C atoms, alkoxy groups having 1 to 5 C atoms or phenoxy groups; benzyl or phenylethyl groups which are unsubstituted or substituted by fluorine atoms, nitro groups, alkyl groups having 1 to 5 atoms, alkoxy groups having 1 to 5 C atoms or phenoxy groups; alkoxy groups having 1 to 5 C atoms; phenoxy groups which are unsubstituted or substituted by fluorine atoms, nitro groups, alkyl groups having 1 to 5 C atoms, alkoxy groups having 1 to 5 C atoms or phenoxy groups; or, together with the nitrogen atom, a five or six-member non-aromatic ring which can be broken by an oxygen or sulphur atom; $R_1'$ additionally represents hydrogen, or $R_1'$ represents hydrogen and $R_2'$ represents a group of the formula:

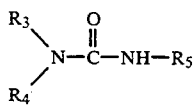 III in which $R_3$ and $R_4$ have the meanings of $R_1'$ and $R_2'$ as described above, whereby $R_3$ and $R_4$ additionally represent hydrogen, and $R_5$ represents an alkylene group with 2 to 20 C atoms or an alkylene phenylene alkylene group, in which the alkylene groups independently of one another have 1 to 3 C atoms, comprising reacting a urea or a bis urea of the formula:

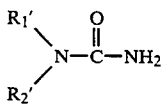 IV in which $R_1'$ and $R_2'$ have the meaning as described above in the presence of a solid base and a phase-transfer catalyst in a diluting agent which is inert under reaction conditions at temperatures of 0° to 150° C. with a compound of the formula:

$$X-R_6-X \qquad V$$

in which $R_6$ represents a straight-chain alkylene group with 4 or 5 C atoms in which the C atom can be replaced in the 2 or 3 position by an oxygen or sulphur atom, and X represents a halogen, sulphonic acid, or hydrogen sulphate leaving group, whereby the —$NH_2$ group of the urea of the formula IV is dialkylated by elimination of both hydrogen atoms through the compound of the formula V by elimination of the X leaving groups through ring closure.

2. The method as claimed in claim 1, comprising employing a urea of the formula IV in which $R_1'$ and $R_2'$ represent independently of one another a straight-chain alkyl group with 1 to 8 C atoms, and $R_1'$ additionally represents hydrogen, or $R_1'$ and $R_2'$ represent together with the nitrogen atom a 5- or 6-member non-aromatic ring which can be broken by an oxygen atom.

3. The method as claimed in claim 1, comprising employing a compound of the formula V in which X represents a halogen atom.

4. The method as claimed in claim 1, comprising employing an aromatic hydrocarbon as the diluting agent.

5. The method as claimed in claim 1, comprising employing potassium or sodium hydroxide as the base and a quaternary ammonium salt as the phase-transfer catalyst.

* * * * *